US009804089B2

(12) United States Patent
Bruls et al.

(10) Patent No.: US 9,804,089 B2
(45) Date of Patent: Oct. 31, 2017

(54) SENSING DEVICE FOR DETECTING A TARGET SUBSTANCE (75) Inventors: Dominique Maria Bruls, Heeze (NL); Toon Hendrik Evers, Eindhoven (NL); Johannes Joseph Hubertina Barbara Schleipen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1585 days.

(21) Appl. No.: 13/201,927

(22) PCT Filed: Feb. 8, 2010

(86) PCT No.: PCT/IB2010/050553
§ 371 (c)(1),
(2), (4) Date: Oct. 27, 2011

(87) PCT Pub. No.: WO2010/095071
PCT Pub. Date: Aug. 26, 2010

(65) Prior Publication Data
US 2012/0040475 A1 Feb. 16, 2012

(30) Foreign Application Priority Data

Feb. 18, 2009 (EP) ..................................... 09153105

(51) Int. Cl.
*G01N 21/552* (2014.01)
*G01N 33/543* (2006.01)
*G01N 21/27* (2006.01)

(52) U.S. Cl.
CPC ..... *G01N 21/552* (2013.01); *G01N 33/54373* (2013.01); *G01N 21/274* (2013.01)

(58) Field of Classification Search
None
See application file for complete search history.

(56) References Cited

U.S. PATENT DOCUMENTS

| 5,485,277 A | 1/1996 | Foster |
| 7,317,534 B2 | 1/2008 | Kimura |
| (Continued) | | |

FOREIGN PATENT DOCUMENTS

| EP | 1645880 A1 | 4/2006 |
| EP | 1712285 A1 | 10/2006 |
| (Continued) | | |

OTHER PUBLICATIONS

Andreas Otto, "Excitation of Nonradiative Surface Plasma Waves in Silver by the Method of Frustrated Total Reflection", Zeitschrift fur Physik, 216, pp. 398-410, (1968).

*Primary Examiner* — Melanie Y Brown
*Assistant Examiner* — Richard Moerschell (57) ABSTRACT A sensing device (100) detects a target substance (2) in an investigation region (113). The sensing device (100) includes a sensing surface (112) with an investigation region (113) and a reference region (120). The sensing device (100) further includes a reference element (121) located at the reference region (120). The reference element (121) is adapted to shield the reference region (120) from the target substance (2) such that light reflected at the reference region (120) under total internal reflection conditions remains unaffected by the presence or absence of the target substance (2). This allows measuring a property, typically the intensity, of light reflected at the reference region (120) independent of the presence or absence of the target substance (2). This measured property of the reflected light can be used for performing a correction of light reflected at the investigation region (113).

15 Claims, 7 Drawing Sheets

(56) References Cited

U.S. PATENT DOCUMENTS

| | | | |
|---|---|---|---|
| 7,413,893 B2 | 8/2008 | Schermer | |
| 2002/0171841 A1* | 11/2002 | Elkind | G01N 21/553 |
| | | | 356/445 |
| 2004/0046963 A1* | 3/2004 | Lackritz | G01N 21/253 |
| | | | 356/445 |
| 2005/0052655 A1 | 3/2005 | Jones | |
| 2005/0200852 A1 | 9/2005 | Kimura | |
| 2006/0073609 A1* | 4/2006 | Shimizu | G01N 21/05 |
| | | | 436/180 |
| 2006/0139641 A1 | 6/2006 | Gollier | |
| 2006/0238766 A1* | 10/2006 | Polwart | G01N 21/553 |
| | | | 356/445 |
| 2007/0004030 A1* | 1/2007 | Ogura et al. | 435/287.2 |
| 2007/0109541 A1 | 5/2007 | Imato | |
| 2010/0248351 A1* | 9/2010 | Seyama | B01L 3/502715 |
| | | | 435/288.7 |

FOREIGN PATENT DOCUMENTS

| | | |
|---|---|---|
| JP | 09257699 A | 10/1997 |
| WO | 0208762 A1 | 1/2002 |
| WO | 03056296 A2 | 7/2003 |

* cited by examiner

SENSING DEVICE FOR DETECTING A TARGET SUBSTANCE

FIELD OF THE INVENTION

The present invention relates to a sensing device and an analyzing device for sensing a target substance in an investigation region. The invention further relates to a corresponding sensing method for sensing a target substance in an investigation region.

BACKGROUND OF THE INVENTION

U.S. Pat. No. 7,317,534 B2 provides a measuring method comprising a measuring unit with a film layer having a detecting area where a target molecule is fixed to the surface thereof and a reference area where no ligand is fixed to the surface thereof. A photo detector detects the intensities of light beams reflected in total internal reflection at the detecting area and reference area, respectively. Further, the result of measurement in the detecting area is calibrated on the bases of the result of measurement in the reference area.

US2005/0052655 A1 describes an interferometer comprising an optical body adapted in operation to mount a measurement area comprising a film which is capable of acting as a two dimensional environment for surface plasmons and an adjacent reference area, an optical beam generation means for irradiating the reference and measurement areas with radiation capable of generating surface plasmon resonance, optical means for combining radiation reflected from the reference and measurement areas, and pixelated detection means for generating data representing two dimensional images of the combined radiation beams.

SUMMARY OF THE INVENTION

However, it is frequently difficult to guarantee that a reference area remains free of any target molecule or otherwise unaffected by the presence of the target molecule in the medium. Particularly when employing bead-based target molecule detection systems, it is difficult to ascertain that no such beads unspecifically come into contact with the reference area and influence the signal detected from the reference area. Thus, measures must be provided for ensuring that the reference area remains free of any target molecule during calibration, which renders the calibration procedure quite complicate.

It is an object of the invention to provide a sensing device and an analyzing device for detecting a target substance in an investigation region that allow for easier calibration. It is a further object of the present invention to provide a corresponding sensing method.

In an aspect of the present invention a sensing device for detecting a target substance in an investigation region is provided, comprising
  a sensing surface with an investigation region and a reference region thereon,
  a reference element located at the reference region adapted to shield the reference region from the substance such that light reflected at the reference region under total internal reflection conditions remains unaffected by the presence or absence of the substance.

The invention is based on the idea that a signal corresponding to the presence of a substance at the investigation region obtained by detecting light reflected from the investigation region under total internal reflection conditions can be calibrated by a signal corresponding to a standard reflecting light under total internal reflection conditions. Thus, a reference element effectively shielding the reference region from the influence of substances potentially present at the investigation region allows to measure a property, typically the intensity, of light reflected at the reference region in a standardized form, i.e. not dependent on the presence or absence of the substance to be analysed. Thus, the light reflected at the reference region is substantially only a function of factors other than the presence or absence of the substance and thus reflects errors due to measurement errors, e.g. increases in temperature or fluctuations in the light output reaching the reference region.

Within the present invention, light reflected at the reference region under total internal reflection conditions is considered unaffected by the presence or absence of the substance when a selected property of the light, typically its intensity, is not altered by the presence or absence of the substance by more than 10%, preferably not more than 1%, and most preferably not more than 0.1%. Particularly preferred is a range of 0.05 to 0.3%.

Further preferably, the reference element shields the reference region not only from the substance to be analysed, but also against other substances potentially influencing an evanescent field present at the reference region. This advantageously allows to analyse the presence of a substance in a coloured medium, as the coloration of the medium would not interfere with the light reflected at the reference region under total internal reflection conditions. Thus, even for coloured media the reference region can serve as a reliable standard. The method of the present invention and the sensing devices of the present invention can also advantageously be used to complement analytical methods involving measurement of transmitted light, for example measurement of light absorption and optical density. It is thus advisable for the reference element to be preferably solid, gel-like or otherwise resistant against being washed away by the medium.

It should be noted that the term "total internal reflection" shall include the case frequently termed "frustrated total internal reflection", where some of the incident light is lost during the reflection process. The reflected light beam originating at the investigation region will typically consist of or comprise light of the incident light beam that was totally internally reflected at the investigation region of the sensing surface, which might be a binding surface for binding the target substance. It may, however, also comprise light from other sources like a fluorescence stimulated in the investigation region.

The refractive index and dimensions of the reference element are preferably chosen such that the dimensions exceed the exponential decay length of an evanescent field elicited therein, i.e. such that the evanescent field is substantially not located outside of the reference element and of a carrier on which the reference element is located. The thickness and lateral dimensions of the reference element are then chosen in such a way that the evanescent field generated under total internal reflection conditions inside the reference element is substantially damped out for a chosen wavelength and angle of incidence of light. The exponential decay length $\zeta$ scales as $$\zeta = \frac{\frac{\lambda}{n_1}}{2\pi\sqrt{\sin^2(\theta) - \sin^2(\theta_{crit})}} \text{ with} \tag{1}$$

$$\theta_{crit} = \sin^{-1}\left(\frac{n_2}{n_1}\right), \tag{2}$$

wherein $\lambda$, and $\theta$ are the wavelength of the used light and the angle of incidence, respectively, and $n_1$ and $n_2$ are the refractive indices of the material the light travels in and of the reference element, respectively. The angle $\theta_{crit}$ defines the critical angle. Thus, the skilled person can select suitable materials for manufacturing of the reference element for a preselected wavelength, angle of incidence and material for the light ray to travel in.

The lateral shape of the reference element can be chosen arbitrarily, thus allowing the present device to be adapted to a plethora of ancillary conditions. Preferably, the reference element is a film or layer having a thickness of at least 200 nm, more preferably 500 nm-1 mm and most preferably 500 nm-100 µm. Such elements advantageously can be included in microsensors allowing to analyse minute quantities of a medium.

In a further preferred sensing device, the investigation region comprises a binder for binding a target. The target can be a target substance which can influence an evanescent field on its own. However, in case the substance whose concentration is to be determined requires a label to influence an evanescent field for its detection—hereinafter termed "analyte"—, the target would be such label. Typically, the target will then be a substance, preferably a magnetic bead, comprising a coupling section to attach to the analyte, preferably by an attachment specific for the analyte in view of other substances that are expected to be further comprised in the medium. The coupling section may be linked covalently or non-covalently to the analyte and the rest of the target substance, respectively. Preferably, the target comprises one, two, three or more antibodies or Fab fragments thereof, including $F(ab')_2$ fragments, which can bind to the analyte at the same or at different sections of the analyte.

A typical example of a binder of the investigation region is an antibody or Fab fragment thereof, including $F(ab')_2$ fragments. Such binders can be produced for a huge variety of target molecules and antigens thereof and allow for the specific binding of targets and/or analytes, where applicable, at the investigation region of the sensing surface. It is thus possible to selectively enrich these targets/analytes at the investigation region. Moreover, undesired targets can be removed from the investigation region by suitable repelling forces (e.g. magnetic or hydrodynamic forces) that should not substantially break the binding between desired target molecules and binders. Binding of the target may influence the evanescent field elicited at the investigation region and thus influence the intensity of light reflected therefrom under total internal reflection conditions. Also further substances may be added to augment the influence exerted by a bound target at the investigation region on the evanescent field elicited thereon. Further, the investigation region may comprise one, two or more types of binders. The types of binders can be specific for different target molecules or for different sections and antigens of one or more target molecules. The sensing surface of the present invention is thus suitable for different kinds of bio sensors and measuring methods.

Another type of assay for determining the concentration of an analyte in a medium can be a competitive binding assay. In such assay, quantitation of an analyte concentration can be achieved by analysing the presence or absence of a target at a respective investigation region as a result of a competition between the analyte and an analyte-like substance for binding by the binder and/or the target or its respective coupling section.

The sensing device of the present invention is preferably adapted to analyse the presence of a substance (i.e. target or, if applicable, analyte) in a medium at a concentration of less than or equal to 1 nM, even more preferably from 1 to 1000 pM and most preferably from 10 to 1000 fM. Such low concentrations typically require long measuring times and the obtained signals from the medium are small as well. The signals generated by typical optical sensor devices can drift over time with no changes in assay composition. For example, the light output of the light source may vary, e.g. due to temperature changes of the environment or within the biosensor device. The drift can lead to significant deviations of the obtained signal compared to the real amount of target molecules bound at the investigation region. Thus, a calibration of the signal obtained by the detector from the investigation region is necessary to obtain significant results. It is a particularly valuable advantage of the present invention to allow such calibration based on the reference region and light reflected thereat, such allowing to reliably analyse the presence or absence of a substance at the low concentrations mentioned before. This is particularly advantageous when measuring the presence of substances like e.g. cardiac Troponin-I, parathyroid hormone (PTH) and BNP (brain natriuretic peptide), in physiological samples, e.g. blood, which require detection limits of less than 1 pM.

In a preferred sensing device the sensing surface at the reference region is tilted relatively to the sensing surface of an investigation region to allow incidence of an incident light beam at the reference region at an angle shallower than that of a parallel incident light beam at the investigation region. To achieve total internal reflection conditions at the sensing surface-reference element interface, the refractive index of the reference element material must be chosen low enough for a given refractive index of the material the reflected light travels in. For some materials it is thus difficult to find a suitable reference element material. By slightly tilting the surface at the reference region, it is possible achieve an angle of incidence shallower at the reference element than at an investigation area, thus allowing to use reference element materials with comparatively higher refractive index.

In a further preferred sensing device, the reference region is preferably adjacent to the investigation region. This way, errors in intensity measurements of light reflected under total internal reflection conditions e.g. due to slight variations in the carrier material compositions can be minimized. Within the present invention, a reference region is considered adjacent when it is separated from an investigation region, preferably an investigation region having attached a binder thereto as described above, by at most 5 mm, more preferably 0.5 to 1 mm, and most preferably 0.1 to 0.5 mm.

The material of the reference element can be chosen arbitrarily, as long as it allows total internal reflection at the reference region for a preselected wavelength and angle of incidence of light and sufficiently shields the reference region as indicated above. Preferably, the reference element is a solid, even more preferably the reference element is a film. Within the present invention, glasses are considered solids. Further preferred materials of the reference element are chosen from polymers, biomolecules and particularly proteins, nucleic acids and polysaccharides, gels, sol-gels and other plastics.

It is preferred to choose a material that can be deposited in a simple way, e.g. ink-jet printing. Many polymers are available that can be UV-cured or be polymerized by other suitable means for fast, reliable and automated polymerization.

It is further preferred that the reference region comprises a mirror to reflect incident light. Such mirror, frequently termed true mirror, can be applied in the form of a dielectric multilayer or metallic coating and is particularly suitable as a reference element in such conditions where finding a reference element material with sufficiently low refractive index is difficult.

In many practically relevant embodiments of the sensing device, the sensing surface will comprise two or more investigation regions at which different incident light beams can be totally internally reflected. One device then allows the processing of several investigation regions and thus for example the search for different target substances, the observation of the same target substances under different conditions and/or the sampling of several measurements for statistical purposes. The "different incident light beams" may optionally be components of one broad light beam that is homogeneously generated by one light source, they may be individual separate light beams addressing the investigation regions and/or reference regions simultaneously (optionally through the same or through different optical windows), and/or they may be temporally different (i.e. be generated by one generic light beam scanning the investigation regions). Preferably, the "different incident light beams" are part of one broad light beam simultaneously illuminating the one, two or more reference region(s) and the one, two or more investigation region(s). A detector may then measure the light reflected from the respective regions separately, als will be described in greater detail below.

The sensing device preferably is a cartridge having a carrier comprising the sensing surface thereon. Such cartridges can be advantageously used with analyzing devices, to adapt the analyzing devices to specific measurement tasks.

While it is in principle possible that the carrier has some dedicated structure with multiple components of different materials, it is preferred that the carrier is homogenously fabricated from a transparent material, for example from glass or a transparent plastic. The carrier can thus readily be produced for example by injection moulding.

The cartridge may be used in combination with many different devices including biosensor devices and methods. For a practically important application in an investigation procedure, the cartridge preferably comprises a first and a second optical window, such that an incident light beam can enter the carrier through the first optical window such that it is totally internally reflected at the investigation region and/or the reference region at the sensing surface, and wherein a reflected light beam originating at the investigation region and/or the reference region can exit the carrier through the second optical window.

The sensing device of the present invention preferably further comprises
  a light source to direct incident light to the investigation region and the reference region of the sensing surface such that the incident light is reflected under total internal reflection conditions at the investigation region and the reference region thereby generating reflected light,
  a detector for detecting the reflected light to yield a first characteristic signal depending on the reflection at the investigation region and a second characteristic signal depending on the reflection at the reference region, and
  a calibrator for calibrating the first characteristic signal in view of the second characteristic signal.

Such device makes use of the advantage of the present invention, i.e. the sensing device allows to calibrate the first characteristic signal in view of the second characteristic signal. The sensing device thus particularly facilitates reliable, significant measurements, limits measurement errors and allows detecting a target substance at the investigation region(s) at low concentrations by enabling long(er) measurement times.

In practical embodiments of such device, the calibrator is preferably adapted to correct or ameliorate a drift in the first characteristic signal in view of the second characteristic signal. It is an advantage of such device that particularly long measurement times without significant influence of drift can be achieved, thus facilitating or even enabling to detect target substances at low concentrations at an investigation region or against a noisy medium background.

In a preferred embodiment, the sensing device is adapted to cooperate with an analyzing device for detecting the target substance, wherein the analyzing device comprises:
  an analysis region for accommodating the sensing device,
  a light source to direct incident light to the analysis region such that the incident light is directed to the investigation region and the reference region of the sensing surface and such that the incident light is reflected under total internal reflection conditions at the investigation region and the reference region, thereby generating reflected light, when the sensing device is accommodated in the analysis region,
  a detector for detecting the reflected light to yield a first characteristic signal depending on the reflection at the investigation region and a second characteristic signal depending on the reflection at the reference region,
  a calibrator for calibrating the first characteristic signal in view of the second characteristic signal.

In a further aspect of the present invention there is provided an analyzer device for detecting a target substance, adapted to cooperate with a sensing device for detecting the target substance, wherein the sensing device comprises:
  a sensing surface with an investigation region and a reference region thereon,
  a reference element located at the reference region adapted to shield the reference region from the target substance such that light reflected at the reference region under total internal reflection conditions remains unaffected by the presence or absence of the target substance,
wherein the analyzing device comprises:
an analysis region for accommodating the sensing device,
  a light source to direct incident light to the analysis region such that the incident light is directed to the investigation region and the reference region of the sensing surface and such that the incident light is reflected under total internal reflection conditions at the investigation region and the reference region, thereby generating reflected light, when the sensing device is accommodated in the analysis region,
  a detector for detecting the reflected light to yield a first characteristic signal depending on the reflection at the investigation region and a second characteristic signal depending on the reflection at the reference region,
  a calibrator for calibrating the first characteristic signal in view of the second characteristic signal.

Such an analyzer device is advantageously adapted to a sensing device, particularly a cartridge, of the present invention and makes use of the reference region for calibrating a characteristic signal obtained from the investigation region. The characteristic signal preferably is a light intensity signal. The sensing device preferably is a biosensor.

Again, the calibrator is preferably adapted to correct or ameliorate a drift in the first characteristic signal of light emanating from an investigation region of the sensing device, particularly a cartridge, in view of the second characteristic signal of light emanating from a reference region of the sensing device.

Thus, the analyzer device allows to reduce the measurement error for light intensity measurements at the investigation region. It is thus possible to analyze light reflected from the investigation region for a long period of time without significantly tainting the first characteristic signal obtained from said investigation region by erroneous light intensity drifts. Such analyzing device thus facilitates detection of substances at an investigation region at the very low concentrations which typically require a long irradiation time of the investigation region.

According to a further aspect of the invention there is provided a sensing method for detecting a target substance in an investigation region, comprising the steps of
providing a sensing surface with an investigation region and a reference region thereon,
providing a reference element located at the reference region adapted to shield the reference region from the target substance such that light reflected at the reference region under total internal reflection conditions remains unaffected by the presence or absence of the target substance,
illuminating the investigation region and the reference region under total internal reflection conditions.

The sensing method can further comprise the steps of:
a) irradiating an investigation region of a sensing device of the invention with light and obtaining a first characteristic signal of totally internally reflected light therefrom,
b) before, during or after step a) irradiating a reference region of the sensing device of the present invention with light and obtaining a second characteristic signal of totally internally reflected light therefrom,
c) calibrating the first characteristic signal obtained in step a) by the second characteristic signal obtained in step b).

The sensing method allows to detect the presence of a target substance at an investigation region, and also allows to determine another property of the investigation region, e.g. to determine a temperature by analysing the influence of a thermochromic substance on the intensity of light reflected under total internal reflection conditions at the investigation region.

Preferably, steps a) and c), steps b) and c) or steps a), b) and c) are repeated. Such repetition can be performed for one investigation region to allow a time-resolved analysis of target substance binding at the investigation region. The steps can also be repeated by applying them sequentially to different investigation regions, allowing to determine the amount of target substance(s) bound at different investigation regions.

It is particularly preferred to at least perform steps a) and b) simultaneously for at least one reference region and one investigation region. This way, the calibration can be performed with very low measurement errors.

Further preferred is a sensing method, comprising
i) providing an analyzing device of the present invention,
ii) providing a sensing device, preferably a cartridge, of the present invention at an analysis region of said analyzing device,
iii) binding a target substance at an investigation region of said sensing device,
iv) performing the measuring method steps a), b) and c) as described above.

Such method exploits the advantages of the present invention and particularly allows analysis of a target substance at a very low concentration at an investigation region as described above.

It shall be understood that the sensing device of claim 1, the analyzer device of claim 12 and the sensing method of claim 14 have similar and/or identical preferred embodiments as defined in the dependent claims. It shall further be understood that a preferred embodiment of the invention can also be any combination of the dependent claims with the respective independent claim.

DETAILED DESCRIPTION OF EMBODIMENTS

Figure 1:
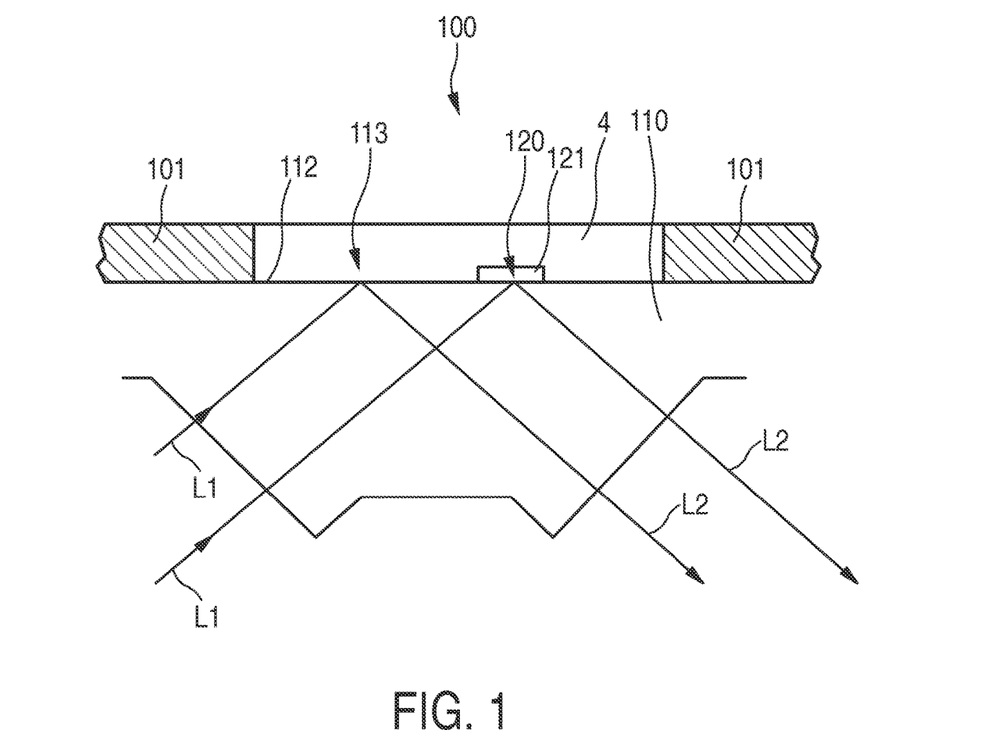
FIG. 1 shows schematically and exemplarily a side view of an embodiment of a sensing device.

FIG. 1 shows schematically and exemplarily a side view of an embodiment of a sensing device 100 of the present invention. The device 100 comprises a carrier 110 of a material transparent for an incident light beam L1. The carrier 110 has a sensing surface 112. On the sensing surface 112, a fluid delimiter 101 is positioned such as to allow a medium 4 to be added to the sensing surface 112. An area of the sensing surface 112 is covered by a reference element 121 to shield a reference region 120 of the sensing surface 112 from any target substance (2) in the medium 4. In the vicinity of the reference region 120 is an investigation region 113 of the sensing surface 112. The investigation region 113 can comprise a binder 114 for direct or indirect binding of the target substance 2.

Both the reference region 120 and the investigation region 113 can be illuminated by incident light (shown as incident light beam L1). The incident light L1 is reflected under total internal reflection conditions at the reference region 120 to produce outgoing light L2. The reference element 121 has such refractive index and such dimensions that an evanescent field elicited by total internal reflection at the reference region 120 remains unaffected by the presence or absence of the target substance 2. Thus, the intensity of the outgoing light beam L2 of the reference region 120 does not depend on the presence or absence of the target substance 2 in the medium 4, and is preferably also independent of the presence or absence of other substances of the medium 4. The outgoing light beam L2 of the reference region 120 can then serve as a standard light beam, and its intensity can be used as a (second) characteristic signal 220 at a detector 18.

The incident light L1 is also reflected under total internal reflection conditions at the investigation region 113 to produce further outgoing light L2. However, an evanescent field elicited at the investigation region 113 is subject to influences of the target substance 2 of the medium 4, and most preferably only or mainly of the target substance 2. The intensity of such further outgoing light then correlates with the presence or absence of the target substance 2 at the investigation region 113 and can serve as a (first) characteristic signal 213 at the detector 18.

A calibrator 20 compares the outgoing light L2 of both the reference region 120 and the investigation region 113. By such comparison the influence of the target substance 2 on the intensity of light reflected at the investigation region 113 under total internal reflection conditions can be determined. This mode of comparison reduces or eliminates any further sources of measurement error, as the comparison can be made largely independent of the variation in incident light L1 intensity by simultaneous or sequentially swift measurement of the intensity of outgoing light L2 of the reference region 120 and the investigation region 113. Also, both first and second characteristic signal 213 and 220, respectively, can be determined at a single detector 18, further reducing measurement errors. The calibrator 20 thus effectively corrects or ameliorates a drift in the first characteristic signal 213 in view of the second characteristic signal 220.

Figure 8:
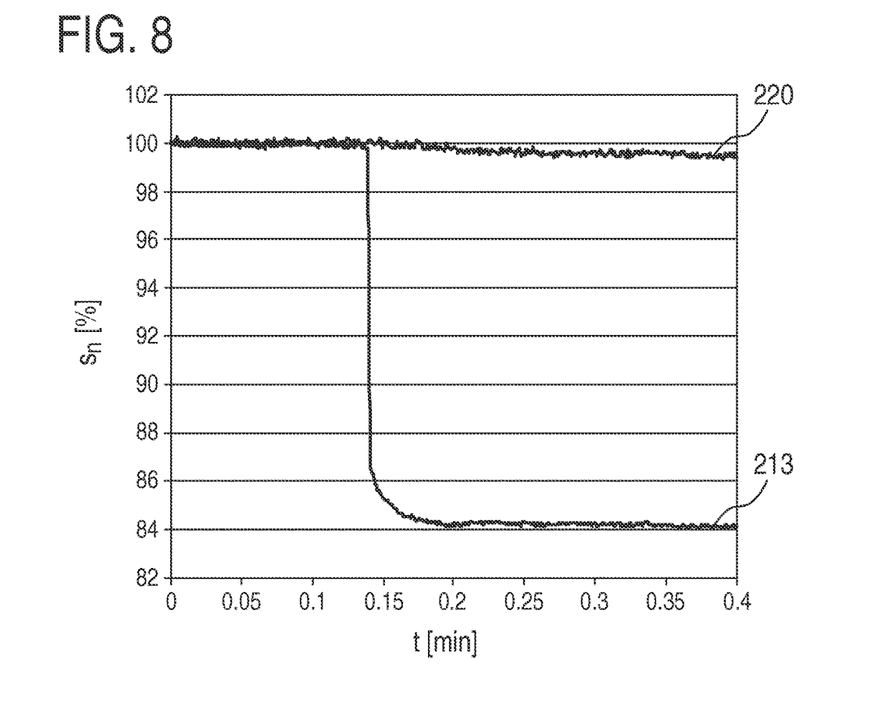
FIG. 8 shows schematically and exemplarily a graph of a detection signal and a reference signal.

To produce a reference element 121, a small drop of UV-curable, low refractive index acrylate (2,2,3,3,4,4,5,5-Octafluoro-hexanediol-1,6-dimethacrylate) can be applied on a sensing surface 112 of a polystyrene cartridge. After curing under nitrogen conditions, a reference element 121 with $n_2<1.42$ at a reference region 120 can thus be obtained. For such reference element 121 it was found that when an adjacent investigation region 113 of the sensing surface 112 was blackened with a black marker pen, the intensity of light reflected (L2) under total internal reflection conditions (angle of incidence $\theta_i$: 70°) decreased markedly at the investigation region 113. However, even though the reference element 121 was also covered by ink of the black marker pen, the intensity of light reflected under total internal reflection conditions (angle of incidence $\theta_i$: 70°) did not decrease markedly at the reference region 120, as shown in FIG. 8.

The refractive index $n_2$ of the cured acrylate is still rather high. Under the aforementioned special experimental conditions, the incoming beam was not perfectly parallel, such that part of the incident light had a smaller angle than 70°. This means that a small portion of the incoming light beam penetrated the reference element 121 and was thus subjected to the influence of the black marker ink, reducing the intensity of reflected light.

This can be solved by further reducing the refractive index on the reference element 121 and/or by increasing the angle of incidence and/or by increasing the refractive index of the cartridge material and/or by improving the collimation of the incoming illumination beam. Instead of a polymer, other low refractive index materials may be suitable like e.g. biomolecules (particularly proteins, nucleic acids, polysaccharides), gels, sol-gels or other plastics. The way these different reference elements 121 are applied to a sensing surface 112 is dependent on the nature of the reference element 121, the sensing surface 112 and the cartridge material. For example, in case of biomolecules it might be necessary to covalently attach them to the cartridge sensing surface 112.

Figure 2:
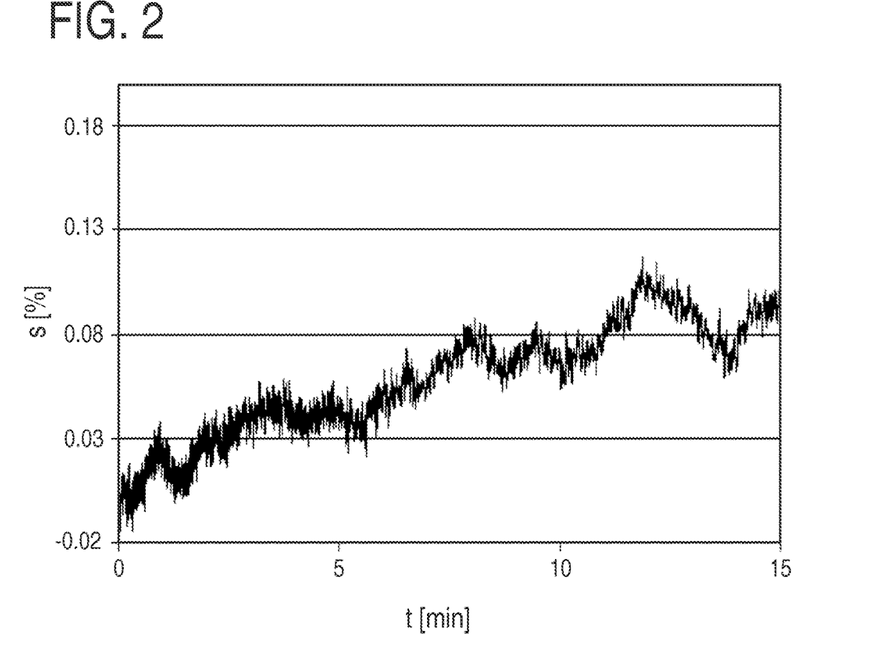
FIG. 2 shows schematically and exemplarily a graph of a signal drift of an uncorrected detection signal.

FIG. 2 shows schematically and exemplarily a graph of a signal drift of an uncorrected detection signal. The x-axis refers to measurement time t given in minutes. The y-axis refers to the variation (given as a percentage) of a first characteristic signal 213 of light of an investigation region 113 of a sensing device 100 of the type of FIG. 1. No substance was added to the investigation region 113 during the measurement of FIG. 2. The graph shows that after 10 minutes of measuring time, the first characteristic signal 213 had drifted by 0.1%. Since this drift was not caused by the addition of a substance to the investigation region 113, the drift must be considered a measurement error. Without being bound to any particular theory, such drift is considered to result from arbitrary variations in the intensity of a light source 11, e.g. a LED, and the sensitivity of a sensor, e.g. a CMOS sensor, particularly due to temperature changes in the device. Such measurement errors cannot be tolerated in analytical tasks requiring high detection sensitivity and precision, e.g. the determination of Troponin-I concentration in a medium 4 like blood. Such analytical tasks can require a detection limit of less than 1 pM which, in turn, require long measuring times with very low signal drift. The device of FIG. 1 now allows to reliably accomplish these analytical tasks.

Figure 3:
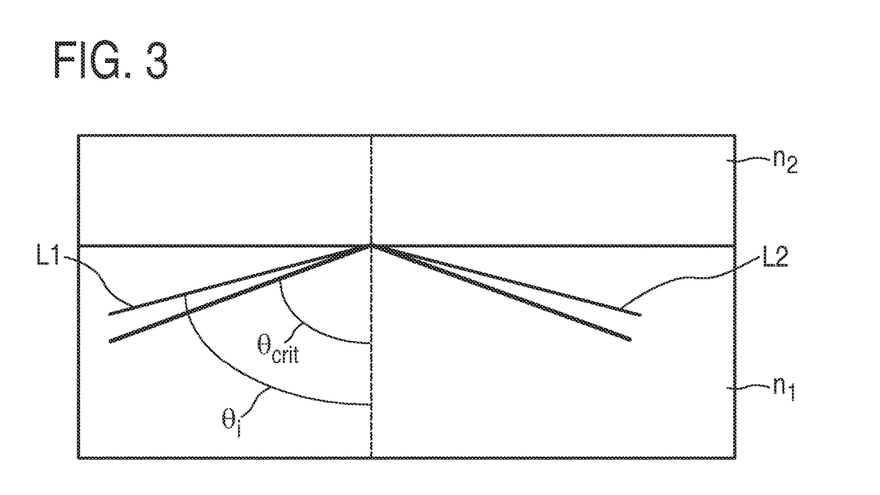
FIG. 3 shows schematically and exemplarily a side view of light reflected under total internal reflection conditions.

FIG. 3 shows schematically and exemplarily a side view of light reflected under total internal reflection conditions and illustrates the principle of total internal reflection. An incident light beam L1 travels through a medium 4 with a first refractive index $n_1$. The light beam L1 reaches a surface to another medium 4 with a second refractive index $n_2$. The light beam L1 is then reflected under total internal reflection conditions to form a light beam L2 if the angle of incidence $\theta_i$ is larger than a critical angle $\theta_{crit}$, where according to Snell's law $\theta_{crit}=\sin^{-1}(n_2/n_1)$.

For example, a material useful for manufacture of biosensor cartridges is polystyrene. For a polystyrene material, $n_1$ is 1.55. Further, when choosing an angle of incidence $\theta_i$ of 70° as would be useful for a biosensor device having a polystyrene/water-like sensor interface, the second medium 4 should be chosen such that $n_2<1.45$. $\theta_{crit}$ would then be 69.1°, such that total internal reflection would occur at the surface between both media.

In preferred sensing devices, some margin is included for $n_2$, as there is frequently some angular distribution in the angle of incidence, e.g. as a LED might not produce perfectly parallel beams. To have an angular margin of 2°, $n_2$ should be chosen to be less than 1.419.

Figure 4:
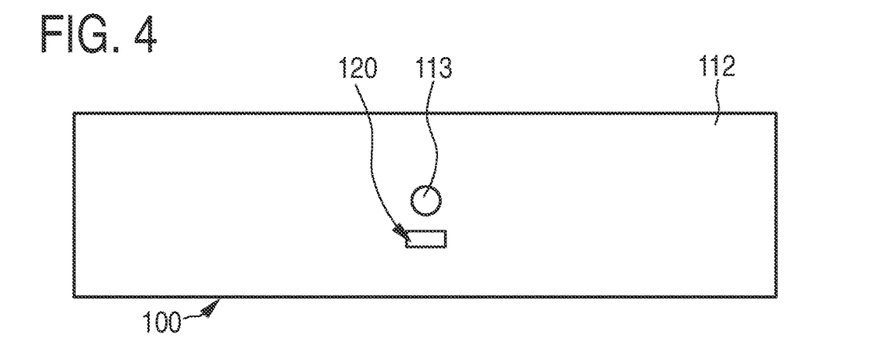
FIG. 4 shows schematically and exemplarily a top view of an embodiment of a sensing device.
Figure 5:
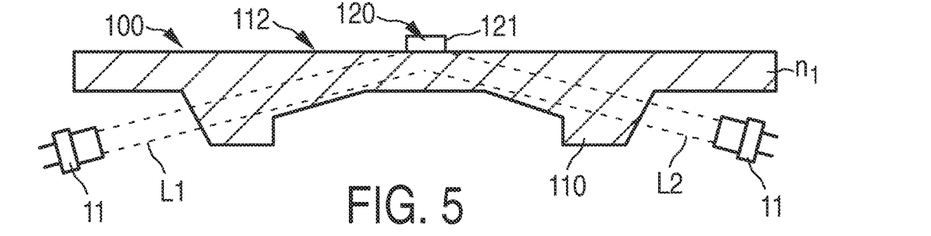
FIG. 5 shows schematically and exemplarily a side view of the embodiment of a sensing device of FIG. 4.

FIGS. 4 and 5 schematically and exemplarily show a top and side view of a sensing device 100, respectively. The sensing device 100 has a cartridge 110 of a first refractive index $n_1$. The cartridge 110 has a sensing surface 112. On the sensing surface 112, a reference element 121 is positioned to shield a reference area 120 of the sensing surface 112. Adjacent to the reference area 120 is an investigation region 113 of the sensing surface 112. The investigation region 113 does not comprise a reference element 121. In FIG. 5, the investigation region 113 is obscured by the reference element 121.

Both the investigation region 113 and the reference region 120 can be illuminated by a beam of incident light L1 of a LED light source 11. The light source 11 can also be a laser diode or Super Luminescent Diode (SLED) or another light source 11. The incident light beam L1 is reflected under total internal reflection conditions at the reference region 120 and, in the absence of an influencing target substance (2), also at the investigation region 113 to form a light beam L2. The light beam L2 is detected at a detector 18 to determine the intensity of light reflected at the reference region 120 and investigation region 113, respectively. A calibrator 20 compares the outgoing light L2 of both the reference region 120 and the investigation region 113 as detailed in the discussion of FIG. 1, and as further detailed in the discussion of FIG. 12.

Figure 6:
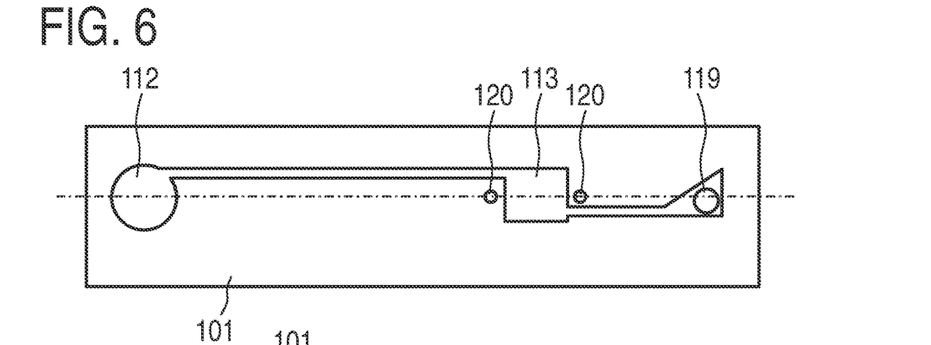
FIG. 6 shows schematically and exemplarily a top view of an embodiment of a sensing device.
Figure 7:
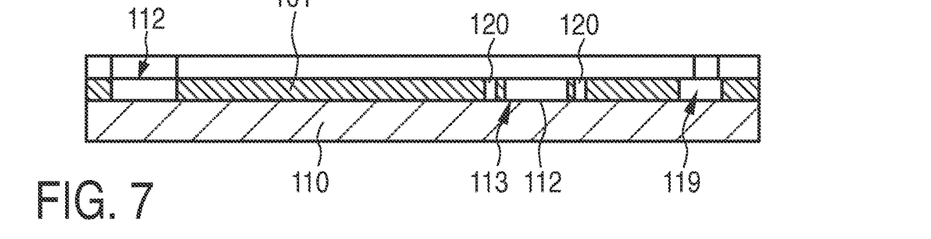
FIG. 7 shows schematically and exemplarily a side view of the embodiment of a sensing device of FIG. 6.

FIGS. 6 and 7 show schematically and exemplarily a top view and side view, respectively, of an embodiment of a sensing device 100. The sensing device 100 comprises a carrier 110. The carrier 110 has a sensing surface 112. On the sensing surface 112, a fluid delimiter 101 is positioned such as to allow a preferably liquid medium 4 to be added to the sensing surface 112. The fluid delimiter 101 has openings forming a fluid channel system comprising a fluid reception opening 112, a channel leading to a measurement chamber, a channel leading away from the reference chamber, and a vent opening 119. The measurement chamber comprises an investigation region 113 of the sensing surface 112. Adjacent to the measurement chamber are two reference regions 120, each comprising a solid reference element to allow total internal reflection of incident light in the carrier 110.

In use, the investigation region 113 and one or both of the reference regions 120 are irradiated by an incident light beam (not shown) in the manner depicted in FIG. 1. The light is reflected under total internal reflection conditions at the reference region(s) 120 and/or the investigation region 113. A fluid medium 4, preferably a liquid, is added to the sensing device 100 via fluid reception opening 120. Air contained in the measurement chamber and channel leading thereto is expelled via vent opening 119. The medium 4 is channeled to the measurement chamber. In the measurement chamber, a target substance 2 can influence the intensity of light reflected at the investigation region 113 of the sensing surface 112 under total internal reflection conditions.

The intensities of light reflected under total internal reflection conditions at the investigation region 113 and the reference region(s) 120 are detected by a detector 18. A calibrator 20 compares the outgoing light of both the reference region(s) 120 and the investigation region 113 in the manner described for FIG. 1.

FIG. 8 shows schematically and exemplarily a graph of a detection signal and a reference signal of a device of FIGS. 6 and 7. A normalized signal intensity $s_n$ is graphed. As can be seen, the characteristic signal 220 obtained from light reflected at a reference region 120 of the sensing surface 112 shows some drift in signal intensity. This detected drift in signal intensity can be used to correct and calibrate the characteristic signal 213 obtained from light reflected at the investigation region 113 of the sensing surface 112.

Figure 9:
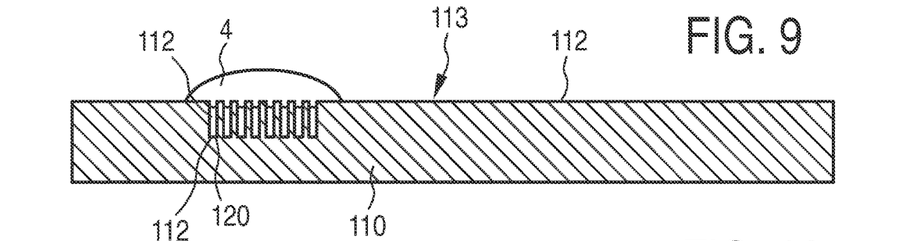
FIG. 9 shows schematically and exemplarily a side view of an embodiment of a sensing device.
Figure 10:
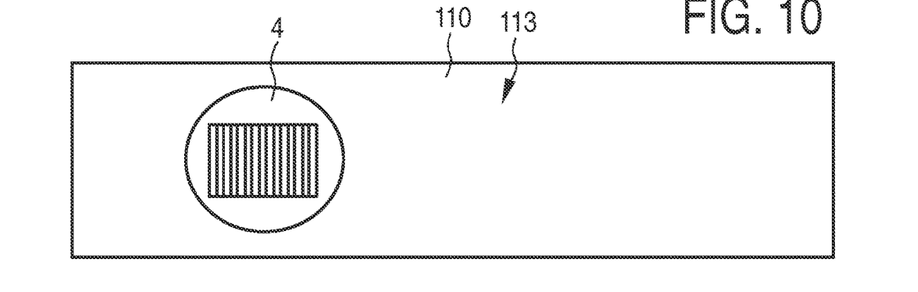
FIG. 10 shows schematically and exemplarily a top view of the embodiment of a sensing device of FIG. 9.

FIGS. 9 and 10 show schematically and exemplarily a side view and top view, respectively, of a further embodiment of a sensing device 100. The device 100 comprises a carrier 110 having a sensing surface 112 thereon. The sensing surface 112 comprises a series of recesses to form a series of lowered reference regions 120 therein. The recesses may be formed by surface patterning, e.g. by using focus ion beam milling or pulsed laser ablation. Adjacent to the reference areas 120 is an investigation region 113 as described with regards to FIG. 1.

In use, a liquid medium 4 passes over the sensing surface 112 of the carrier 110. For purposes of illustration, only a droplet of medium 4 is shown in FIGS. 9 and 10. The medium 4 cannot enter the recesses at the reference region 120 due to its surface tension, entrapping air between the medium droplet 4 and the reference region 120. The air then functions as reference element 121 as described regarding FIG. 1.

Furthermore, also modifications could be made to a top fluidic part of a device of the type depicted in FIGS. 6 and 7 such as to cause air bubbles to be trapped at predefined areas, preferable inside or close to the fluidic channel. Such trapped air bubbles would then function as reference element 121 as described regarding FIG. 1.

Figure 11:
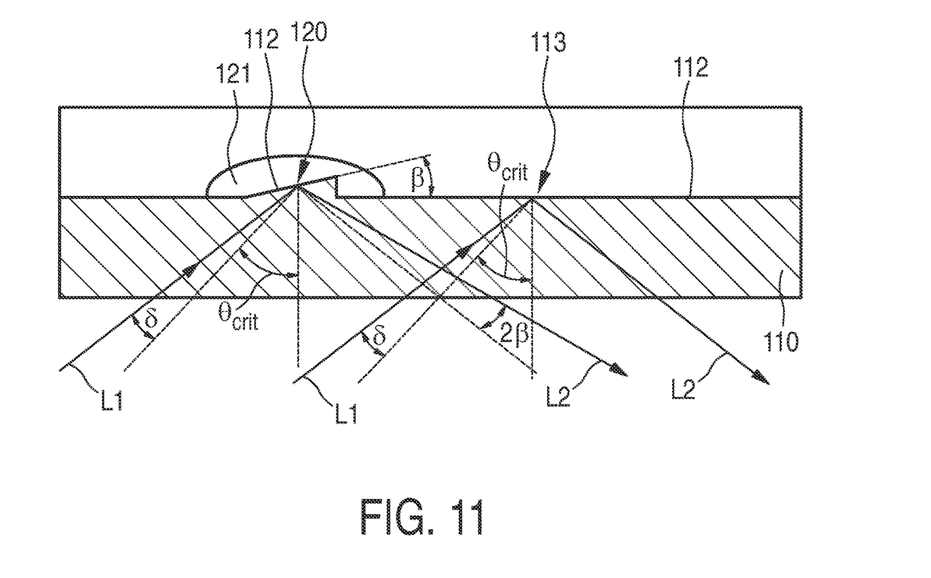
FIG. 11 shows schematically and exemplarily a side view of an embodiment of a sensing device.

FIG. 11 shows schematically and exemplarily a side view of a further embodiment of a sensing device 100. The device comprises a carrier 110 having a sensing surface 112 formed thereon. The sensing surface 112 comprises an investigation region 113 as described for FIG. 1, and a reference region 120. The sensing surface 112 of the reference region 120 is tilted relative to the sensing surface 112 of the investigation region 113 by an angle of β. Parallel incident light beams L1 reaching both the investigation region 113 and the reference region 120 will thus effectively reach the reference region 120 at an angle of $\theta_{crit}+\beta+\delta$ instead of $\theta_{crit}+\delta$ as for the angle of incidence at the investigation region 113. The constraints regarding the refractive index $n_{TWR}$ of the reference element 121 is then relaxed to approximately $$n_{TWR} < n_2 + (\beta + \delta)\sqrt{1 - \frac{n_2^2}{n_1^2}} \qquad (3)$$

where $n_2$ is the expected refractive index of a medium 4 and $n_1$ is the refractive index of the carrier 110 material. Typically, under such relaxed conditions it is easier to find a suitable material for a reference element 121.

Figure 12:
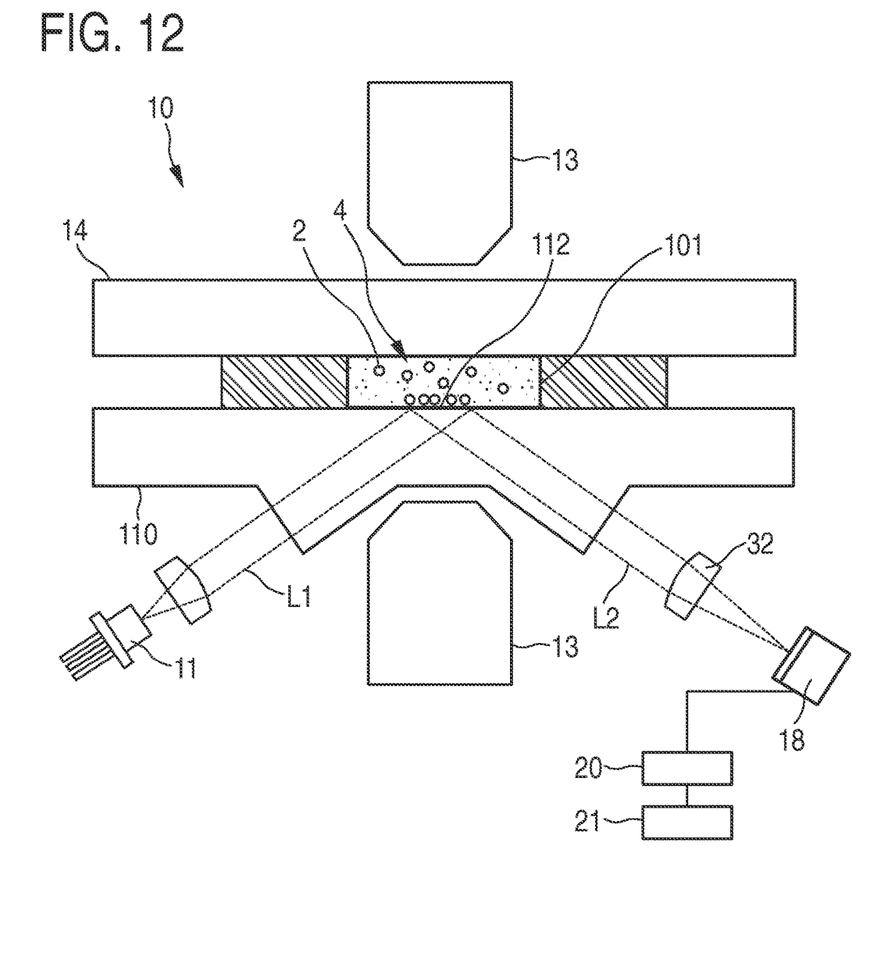
FIG. 12 shows schematically and exemplarily a side view of an embodiment of an analyzing device.

FIG. 12 shows schematically and exemplarily a side view of an embodiment of an analyzer device 10. A sensing device 100 has been inserted in the analyzer device 10. The sensing device 100 comprises, in this embodiment, a carrier 110 having a sensing surface 112 thereon. Further, a fluid delimiter 101 is positioned on the carrier 110. A top fluidic part 14 completes a measuring chamber between the sensing surface 112, the fluid delimiter 101 and the top fluidic part 14.

The analyzer device 10 further comprises a magnetic element 13 which provides a magnetic field for forcing magnetic particles 2 onto the sensing surface 112 of the sensing device. The magnetic particles 2 are detected by, in this embodiment, illuminating the sensing surface 112 with a light beam L1 generated by a light source 11. The light source 11 is, for example, a laser device, SLED or a LED. Light L2 reflected from the sensing surface 112 is detected by a detector 18. The detector 18 is, for example, a photodetector or a two-dimensional camera. Optical elements can be arranged in the light beams L1 and L2 for generating parallel light beams L1 and L2, respectively. Such optical elements are preferably lenses.

The carrier 110 is accommodated in an analysis region. In the analysis region, both incident light L1 can be directed at the reference region 120 and the investigation region 113 such that light reflected under total internal reflection conditions can be detected by the detector 18. Furthermore, at the analysis region the magnetic field created by magnetic element 13 can force magnetic particles 2 onto the sensing surface 112.

The sensing surface 112 further comprises a reference region 120 and an investigation region 113; both are not shown. Incident light L1 arriving at the reference region 120 and investigation region 113 of the sensing surface 112 is reflected under total internal reflection conditions to become a light beam L2. However, at the investigation region 113 such internal reflection may be under frustrated total internal reflection conditions. That is to say that upon movement of magnetic particles 2 onto the investigation region 113, evanescent light present thereat due to the incident light beam L1 is scattered and absorbed, resulting in a change of intensity of light L2 reflected off the investigation region 113. This change can be detected by a detector 18 as described above.

The detector 18 yields two characteristic signals 213, 220. The intensity of light reflected under total internal reflection conditions at the investigation region 113 is yielded as first characteristic signal 213, the intensity of light reflected under total internal reflection conditions at the reference region 120 is yielded as second characteristic signal 220. A calibrator 20 then compares the first characteristic signal 213 and the second characteristic signal 220 to produce a corrected result. The result of the comparison is displayed by a display device 21.

Figure 13:
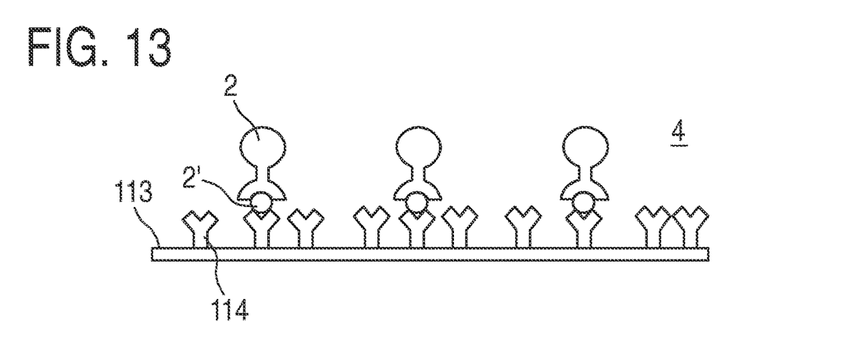
FIG. 13 shows schematically and exemplarily magnetic particles bound to an investigation region of a sensing device.

FIG. 13 shows schematically and exemplarily magnetic beads bound to an investigation region 113 of a sensing device. An investigation region 113 of a sensing surface 112 is coated with antibodies 114. The antibodies 114 can bind an analyte 2'. Further, magnetic beads 2 are coated with antibodies to bind analyte 2'. Upon addition of analyte 2' in a medium 4, analyte 2' is sandwiched between antibodies 114 and magnetic beads 2, thus effectively coupling the magnetic beads 2 to the investigation region 113. The magnetic beads 2 can then influence the light reflected at the investigation region 113 as described with respect e.g. to FIG. 12. The magnetic beads are preferably particles having at least one dimension ranging between 3 nm and 10000 nm, preferably between 10 nm and 3000 nm, and more preferably between 200 nm and 1000 nm.

Figure 14:
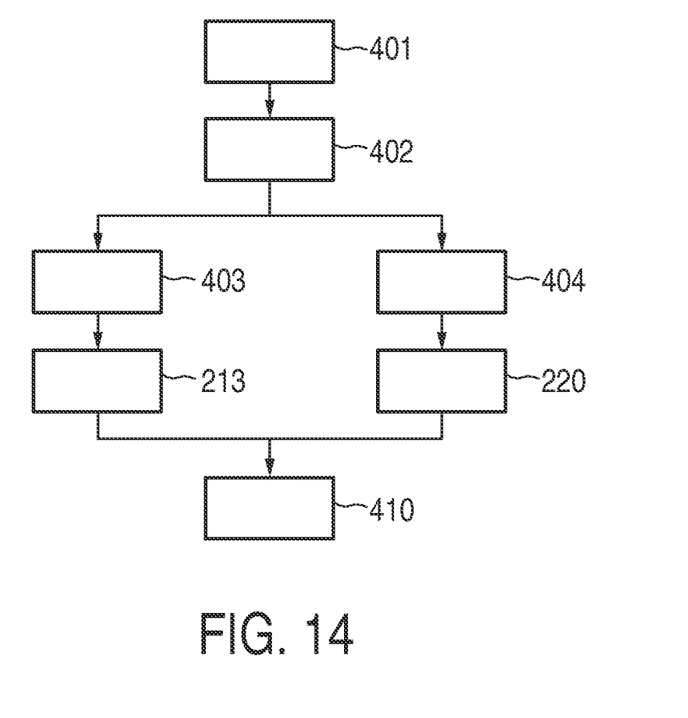
FIG. 14 shows schematically and exemplarily a method of the present invention.

FIG. 14 shows schematically and exemplarily a method of the present invention. In step 401, a sensing surface 112 with an investigation region 113 and reference region 120 is provided. A reference element 121 is located at the reference region 120 to shield the reference region 120 such that light reflected at the reference region 120 under total internal reflection conditions remains unaffected by the presence or absence of a target substance 2 or coloured particulates of a medium 4 comprising the target substance 2 and, where applicable, an analyte. Providing such reference element 121 at the reference region 120 may in some embodiments be performed as an independent method step.

After step 401, the investigation region 113 and the reference region 120 are illuminated under total internal reflection conditions in step 402. A detector 18 detects light reflected from the investigation region 113 (step 403) and the reference region 120 (step 404) under total internal reflection conditions. Steps 403 and 404 can be performed simultaneously, e.g. using a CCD detector. A first characteristic signal 213 is obtained from the detector 18 depending on the light reflected from the investigation region 113. A second characteristic signal 220 is obtained from the detector 18 depending on the light reflected from the reference region 120.

In a further step 410, the first 213 and second 220 characteristic signals are read by a calibrator 20. The calibrator 20 calibrates the first characteristic signal 213 in view of the second characteristic signal 220. A calibrated first characteristic signal 213 is output by the calibrator 20.

In the above described embodiments, the medium 4 was preferably blood. In other embodiments, the fluid can be any other fluid, in particular any other body fluid, for example saliva or urine. The preferred application of the sensing and analyzer device 10 is in the field of point of care diagnostics and detection of drugs or the detection of the occurrence of a heart attack, and in particular based on finger prick blood samples and saliva samples.

The device, methods and systems of this invention are suited for sensor multiplexing (i.e. the parallel use of different sensors and sensor surfaces), label multiplexing (i.e. the parallel use of different types of labels as target substances 2) and chamber multiplexing (i.e. the parallel use of different reaction chambers).

The devices and methods described in the present invention can be used as rapid, robust, and easy to use point-of-care biosensors for small sample volumes. The carrier can be a disposable item to be used with a compact reader, containing one or more magnetic field generating means and one or more detection means. Also, the devices and methods of the present invention can be used in automated high-throughput testing. In this case, the carrier is e.g. a well plate or cuvette type carrier, fitting into an automated instrument.

In the above embodiments, the device uses evanescent field techniques for determining the amount of magnetic particles on the investigation region 113 of the sensing surface 112. In other embodiments, other substances may be detected. In addition to molecular assays, also larger moieties can be detected, e.g. cells, viruses, or fractions of cells or viruses, tissue extracts and so on.

In particular, the embodiments have been described with reference to a sandwich assay as described in FIG. 13. However, other assay types can be employed, e.g. binding/unbinding assay, sandwich assay, competition assay, displacement assay, enzymatic assay, etc.

The target substance 2 may be directly analyzed by its presence on the investigation region 113 without use of magnetic beads. This is particularly preferred for target substances 2 with a high ability to absorb or scatter light of an evanescent field on the investigation region 113. In addition or alternatively thereto, the target substance 2 can be further processed prior to detection. An example of further processing is that further materials are added or that the (bio)chemical or physical properties of the target substance 2 are modified to facilitate detection. The target substance 2 may for example be reacted with a reactant to alter its ability to absorb or scatter light of an evanescent field on the investigation region 113. In particular, the target substance 2 may be covalently linked to a light absorbing or scattering substance to influence an evanescent field in the investigation region 113.

The detection can occur with or without scanning of the sensor element with respect to the sensing surface 112, in particular the reference region 120 and/or the investigation region 113.

In the above embodiments, the reference element 121 has been described as being an element transparent to incident light but chosen to effect reflection under total internal reflection conditions. However, the reference element 121 may also be a true mirror 121, preferably a metal layer, to reflect incident light. This abolishes the need to select such materials for the manufacture of the reference element 121 that have a sufficient refractive index in view of the refractive index of the sensing surface material and the incident light.

Other variations to the disclosed embodiments can be understood and effected by those skilled in the art in practicing the claimed invention, from a study of the drawings, the disclosure and the appended claims.

In the claims, the word "comprising" does not exclude other elements or steps, and the indefinite particle "a" and "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims shall not be construed as limiting the claim's scope. The figures and embodiments shall not be construed as limiting the claims' scope.

The invention claimed is:

1. A sensing device for detecting a target substance in an investigation region, comprising:
    a carrier including a sensing surface exposed to the target substance, the carrier including an investigation region and a reference region;
    a light source generates an incident light beam directed to reflect at the investigation region and the reference region, thereby generating reflected light;
    wherein the carrier is of a material transparent for the incident light beam,
    a reference element located in contact with the sensing surface at the reference region wherein the reference element shields the sensing surface in the reference region from the target substance such that light reflected at the reference region remains unaffected by a presence or absence of the target substance;
    a calibrator compares an intensity of the totally internally reflected light from both the reference region and the investigation region;
    wherein the calibrator determines an influence of the target substance on the intensity of the light reflected at the investigation region
    wherein the reference element has a refractive index and dimensions such that an evanescent field elicited at the reference region is unaffected by the presence or absence of the target substance;
    wherein the sensing surface at the reference region is tilted relatively to the sensing surface of the investigation region by an angle β to allow incidence of the incident light beam at the reference region to be the angle β shallower than that of a parallel incident light beam at the investigation region and still strike the investigation surface at an angle equal to or greater than a critical angle for total internal reflectance.

2. The sensing device according to claim 1, wherein the target substance includes a bead with a coupling section for coupling to an analyte and the analyte is disposed in a medium in the investigation region.

3. The sensing device according to claim 2, wherein the sensing device senses the presence of a substance in the medium at a concentration of less than or equal to 1 nM.

4. The sensing device according to claim 1, wherein the reference region is disposed adjacent to the investigation region.

5. The sensing device according to claim 1, wherein the reference region comprises a mirror to reflect incident light.

6. The sensing device according to claim 1, wherein the sensing device is a cartridge having a carrier comprising the sensing surface thereon.

7. The sensing device comprising:
    a cartridge including:
        a sensing surface,
        an investigation region receives a fluid containing the target substance, the sensing surface forming one side of the investigation region,
        a reference element disposed directly adjacent the sensing surface such that the fluid containing the target substance does not pass between the reference element and the sensing surface;
    a light source directs an incident light beam toward the sensing surface at an angle for reflection under total internal reflection conditions at the investigation region and at the reference region generating reflected light, the reflected light from the reference region directly adjacent the reference element being not affected by a presence or absence of the fluid;
    a detector detects the reflected light and generates a first characteristic signal depending on the reflection at the investigation region and a second characteristic signal depending on the reflected light from the reference surface abutting the reference element;
    a calibrator calibrates the first characteristic signal in view of the second characteristic signal; and
    wherein the sensing surface at the reference region is tilted relatively to the sensing surface of the investigation region by an angle β to allow incidence of the incident light beam at the reference region to be the angle β shallower than that of a parallel incident light beam at the investigation region and still strike the investigation surface at an angle equal to or greater than a critical angle for total internal reflectance.

8. The sensing device according to claim 7, wherein the calibrator corrects or ameliorates a drift in the first characteristic signal in view of the second characteristic signal.

9. The sensing device according to claim 1, in combination with an analyzing device for detecting the target substance, wherein the analyzing device comprises:
    an analysis region for accommodating the sensing device;
    the light source directs the incident light beam to the analysis region including the investigation region and the reference region of the sensing surface at an angle such that the incident light beam is reflected under total internal reflection conditions at the investigation region and the reference region;
    a detector detects the reflected light and yields a first characteristic signal depending on the reflected light from the investigation region and a second characteristic signal depending on the reflected light from the reference region;
    wherein the calibrator corrects the first characteristic signal based on the second characteristic signal.

10. An analyzer system for detecting a target substance comprising:
    a sensing device including:
        a sensing surface defining an investigation region and a reference region thereon the sensing surface, or the reference region being tilted by an angle β, relative to the sensing surface at the investigation region,
        a reference element located at the reference region shields the reference region of the sensing surface from contacting the target substance such that light reflected at the reference region remains unaffected by a presence or absence of the target substance,
    an analyzer device comprising:
        an analysis region receives the sensing device,
        a light source directs incident light to the analysis region such that the incident light is directed to the investigation region incident light is reflected under total internal reflection conditions at at an angle equal to or greater than a critical angle $\theta_{crit}=\sin^{-1}(n_2/n_1)$, where $n_1$ is the refractive index of the sensing surface and $n_2$ is the refractive index of the target substance and directed to the reference region at an angle $\theta_{crit}-\beta$ thereby generating reflected light, when the sensing device is received in the analysis region, a detector detects the reflected light and outputs a first characteristic signal depending on the light reflected by the investigation region and a second characteristic signal depending on the light reflected by the reference region, a calibrator calibrates the first characteristic signal in view of the second characteristic signal.

11. The analyzer system according to claim 10, wherein the calibrator corrects or ameliorates a drift in the first characteristic signal in view of the second characteristic signal.

12. The sensing device according to claim 7, wherein the reference element has such refractive index and dimensions such that an evanescent field elicited by total internal reflection at the reference element region remains unaffected by the presence or absence of the target substance.

13. The analyzer system according to claim 10, wherein the reference element has such refractive index and dimensions such that an evanescent field elicited at the reference region remains unaffected by the presence or absence of the target substance.

14. A method for detecting a target substance, the method comprising:

directing an incident light beam toward a sensing surface which defines an investigation region and a reference region, the reference region including a reference element disposed to shield the reference region of the sensing surface from contacting the target substance, the sensing surface at the reference region being tilted by an angle $\beta$ relative to the sensing surface at the investigation region;

reflecting incident light from the reference region of the sensing surface under total internal reflection conditions or an angle greater than $\theta_{crit}-\beta$ such that the light reflected from the sensing surface at the reference region is unaffected by a presence or absence of the target substance where $\theta_{crit}$ is an angle above which light is reflected;

reflecting the incident light under total internal reflection conditions at the investigation region or an angle greater than $\theta_{crit}$ such that the reflected light from the investigation region of the sensing surface is indicative of the target substance adjacent the investigation region;

detecting the light reflected from the investigation region and generating a first characteristic signal indicative of the characteristic of the target substance in the investigation region, with a detector;

detecting the light reflected by the reference region and generating a second characteristic signal, with the detector; and calibrating the first characteristic signal in view of the second characteristic signal, with a calibrator.

15. The method according to claim 14, wherein the reference element has such refractive index and dimensions such that an evanescent field elicited at the sensing surface adjacent the reference element remains unaffected by the presence or absence of the target substance.

* * * * *